United States Patent
Edmonds, III et al.

(10) Patent No.: US 6,229,908 B1
(45) Date of Patent: May 8, 2001

(54) DRIVER ALCOHOL IGNITION INTERLOCK

(76) Inventors: Dean Stockett Edmonds, III, 360 Club View Dr.; Jon William Hopta, 1201 Wiesman Ct., both of Great Falls, VA (US) 22066

(*) Notice: Subject to any disclaimer, the term of this patent is extended or adjusted under 35 U.S.C. 154(b) by 0 days.

(21) Appl. No.: 08/837,759

(22) Filed: Apr. 22, 1997

Related U.S. Application Data

(60) Provisional application No. 60/017,053, filed on Apr. 26, 1996.

(51) Int. Cl.[7] .................................................. G06K 9/00
(52) U.S. Cl. ...................... 382/124; 382/124; 382/270; 340/561; 340/825.31; 340/933; 356/326; 356/442
(58) Field of Search ................................ 382/124, 116, 382/121, 125, 126, 127, 207, 270, 274; 356/437, 442, 439, 326; 340/933, 576, 561, 825.31

(56) References Cited

U.S. PATENT DOCUMENTS

| | | | |
|---|---|---|---|
| 4,678,057 | * 7/1987 | Elfman et al. ........................ | 180/272 |
| 4,738,333 | * 4/1988 | Collier et al. ........................ | 180/272 |
| 4,996,161 | * 2/1991 | Conners et al. ...................... | 436/132 |
| 5,067,162 | 11/1991 | Driscoll, Jr. et al. ................... | 382/5 |
| 5,088,817 | 2/1992 | Igaki et al. ............................. | 356/71 |
| 5,134,875 | * 8/1992 | Jensen et al. ......................... | 73/1.03 |
| 5,355,880 | 10/1994 | Thomas et al. ....................... | 128/633 |
| 5,361,758 | * 11/1994 | Hall et al. ............................. | 600/322 |
| 5,372,135 | * 12/1994 | Mendelson et al. ................. | 128/633 |
| 5,376,555 | * 12/1994 | Forrester et al. ..................... | 436/132 |
| 5,383,452 | * 1/1995 | Buchert ................................ | 600/347 |
| 5,435,309 | 7/1995 | Thomas et al. ....................... | 128/633 |
| 5,467,403 | 11/1995 | Fishbine et al. ...................... | 382/116 |
| 5,515,847 | 5/1996 | Braig et al. ........................... | 128/633 |
| 5,546,471 | * 8/1996 | Merjanian ............................ | 382/124 |
| 5,719,950 | * 2/1998 | Osten et al. .......................... | 382/115 |
| 5,743,349 | * 4/1998 | Steinberg ............................. | 180/272 |

OTHER PUBLICATIONS

National Highway Traffic Safety Administration, "Alcohol Ignition Interlock Service Support", *DOT HS 807 923 Final Report*, Dec. 1992.

National Highway Traffic Safety Administration, "Potential for Application of Ignition Interlock Devices to Prohibit Operation of Motor Vehicles by Intoxicated Individuals", *A Report to Congress*, May 1988.

Ott, James "Random Alcohol Tests Proposed", *Aviation Week and Space Technology*, Jan. 11, 1993, p. 33.

Synder, Monroe B. "Institution Response to Changes in Alcohol Limits for Drivers", *Alcohol, Drugs, and Driving*, vol. 7, No. 3–4, 1991, pp. 251–260.

White, Alnisa C., "Paralegal Creates Steering Device to Curb Drunk Driving", *Black Enterprise*, Sep. 1994, p. 22.

(List continued on next page.)

*Primary Examiner*—Matthew C. Bella
*Assistant Examiner*—Sheela Chawan
(74) *Attorney, Agent, or Firm*—Pennie & Edmonds LLP

(57) ABSTRACT

A method and an ignition interlock for preventing operation of equipment when an operator's blood-alcohol content is above a threshold value. The interlock has a blood-alcohol detector that measures intensities of wavelengths of light emerging from a finger. A microprocessor correlates these intensities with the finger's blood-alcohol content, determines whether this content is above a threshold level, and prevents the equipment from operating unless the blood-alcohol content is below the threshold. The interlock also has a fingerprint image generator which reflects light of the finger and scans the fingerprint to form a scanned image. The microprocessor compares this scanned image to a prestored image of a principal operator and compares the two images to determine whether the images match. The fingerprint and blood-alcohol analyses occur substantially simultaneously.

35 Claims, 3 Drawing Sheets

OTHER PUBLICATIONS

*Delaware Division of Motor Vehicles*, "Ignition Interlock Device Program—Policies and Procedures", Aug. 1993.

Foss, Robert D. and others, "Using a Passive Alcohol Sensor to Detect Legally Intoxicated Drivers", *American Journal of Public Health*, vol. 83, No. 4, Apr. 1993, pp. 556–560.

Holubowycz, O.T. and others "A New Method of Breath Testing the General Driving Population", *Journal of Studies on Alcohol*, vol. 52, No. 5, 1991, pp. 474–477.

Kelley, Benjamin "Drunken Driver Detectors", *The New York Times*, Jun. 2, 1994.

Labianca, Dominick A. "The Chemical Basis of the Breathalyzer", *Journal of Chemical Education*, March 1990, vol. 67 No. 3, pp. 259–261.

Morse, Barbara J. and Elliot, Delbert S., "Effects of Ignition Interlock Devices on DUI Recidivism: Findings From a Longitudinal Study in Hamilton County, Ohio", *Crime and Delinquency*, vol. 38, No. 2, Apr. 1992, pp. 131–157.

National Highway Traffic Safety Administration, "Model Specifications for Breath Alcohol Ignition Interlock Devices", *Federal Register*, vol. 57, No. 67, Apr. 7, 1992, pp. 11772–11787.

Interlock Information Sheet "Guardian Interlock Systems".

Biometric Identification, Inc., "BII Announces the Development of the VERIPRINT(TM) 2000!", internet address: http://www. biometricID.com, 1996.

Fingerprint Technologies, Inc., "Fingerprint Technologies", internet address: http://www.fingerprint.com, 1996.

East Shore Technologies, Inc. "East Shore Technologies, Key to the World of Fingerprints", internet address: http://www.east-shore.com, 1996.

\* cited by examiner

DRIVER ALCOHOL IGNITION INTERLOCK

This application claims the benefit of Provisional No. 60/017,053 filed Apr. 26, 1996.

BACKGROUND OF THE INVENTION

The present invention relates to an ignition interlock that positively identifies a principal operator and measures the blood-alcohol content directly from a bodypart of the operator. The interlock prevents operation of equipment in which it is installed.

Drunk driving has claimed about 250,000 lives in the past ten years. Every year drunk drivers injure over 650,000 people. Estimates for property damage and medical expenses exceed twenty four billion dollars annually. Statistic studies have shown that eighty two percent of first time drunk driving offenders are problem drinkers or alcoholics. Moreover, more than seventy percent of drivers with suspended licenses continue to drive without insurance.

To prevent convicted drunk drivers from continuing to drive while intoxicated, several law enforcement programs employ ignition interlocks that are installed in convicted drivers'vehicles to prevent the vehicles from being started while the driver is intoxicated. Known interlock devices connect breath-alcohol analyzers to a vehicle's ignition system.

Systems currently available include Ignition Interlock's LIFESAFER™ and Guardian Interlock System's GUARDIAN INTERLOCK™. These devices include a handheld breath-alcohol analyzer and a data logger that records vehicle activities and test results and the time and date at which each took place. With either of these devices, a driver must pass a breath test by blowing into the device before starting the vehicle. Unless the driver passes the test, the vehicle will not start. The units also conduct tests at random intervals once the vehicle has been started to deter the driver from drinking after engine start and continuing to drive while intoxicated.

Both breathalyzers determine blood-alcohol concentration through a measurement of breath-alcohol concentration. They convert the breath reading by comparing the fraction of the amount of ethanol in the exhaled air with a partition ratio, which is the average ratio of the amount of ethanol in exhaled air to the level of ethanol in blood. This partition ratio is based on 2,100 ml of breath air containing the same weight of ethanol as 1 ml of blood.

Although the partition ratio represents the average, the ratio is not accurate for a large number of individuals. Thus, a disadvantage of breath-alcohol measurement is that significant number of individuals have normal breath-alcohol concentrations notably above or below the partition ratio. This often leads to erroneous determinations of blood-alcohol concentrations that might render false indications of intoxication or non-intoxication for drivers whose normal breath-alcohol levels differ from the average.

Another disadvantage stems from the effects of environmental factors on breathalyzers. Breath fresheners and medical inhalants, for example, contain alcohol. Although this alcohol is not in the blood, the breathalyzer detects it in the breath sample, and the use of fresheners of inhalants may cause unwarranted alcohol-test failures. Also, because breathalyzers determine ethanol content by measuring carbon content in the sample breath, dust, cigarette smoke, and fuel vapors can incorrectly result in the breathalyzer registering a failed alcohol-level test.

More accurate methods of determining blood-alcohol concentration involve spectroscopic blood analysis, such as disclosed in U.S. Pat. Nos. 5,515,847, 5,435,309, and 5,361,758. These approaches conduct a chemical analysis of a subjects blood by measuring light emerging from the subject's tissue, such as a finger. Most methods of spectroscopic analysis prescribe irradiating the subject with infrared light and measuring the light emerging from the other side of the tissue, although the '847 patent also discloses measuring infrared absorption patters from infrared emissions generated by the subject's body. Ignition interlock devices, however, have not been fitted with spectroscopic blood-alcohol analyzers.

A further concern in the operation of ignition interlock devices is that persons other than the driver may take and pass the alcohol concentration test, permitting a drunk driver to operate or continue operating the vehicle and defeating the preventive function of the interlock. To address this concern, the GUARDIAN™ requires a the subject to enter a code of breath pulses after passing a test. A person other than the driver may easily learn this code. As a result, the code requirement does not positively identify the test taker.

A different type of device known in the art for identifying individuals, which has not been employed in ignition interlock devices, electronically scans fingerprints. Such devices are taught, for example, in U.S. Pat. Nos. 5,546,471, 5,467,403, 5,088,817, and 5,067,162. Finger print imaging and recognition devices are sold by Biometric Identification, Inc. and Fingerprint technologies. In known devices, a subject places his or her finger against a light conducting platen. Light is then reflected off the fingertip, and an image of the reflected light is scanned. Image processing algorithms in a computer then compare the scanned image to a prerecorded fingerprint image. Depending on the degree of correlation between different regions of the two images, these images are either considered a match or not. Fingerprint identification software is sold, for instance, by East Shore Technologies, Inc.

An easy to use ignition interlock is needed for acquiring accurate blood-alcohol measurements that are not significantly affected by environmental factors or variable normal breath-alcohol levels. The needed interlock should also positively identify the test subject during the test, to prevent people other than the driver from taking the test.

SUMMARY OF THE INVENTION

The invention relates to an interlock that prevents equipment from being operated when the operator is intoxicated by measuring the blood-alcohol level in a bodypart, such as a finger, and substantially simultaneously determines whether the operator is the convicted or principal operator of the equipment, preferably by scanning the operator's fingerprint and comparing it with a fingerprint image stored in the interlock's memory.

The interlock has a detector unit which houses a spectroscopic blood-alcohol detector and a fingerprint image generator. The blood-alcohol detector operates by measuring intensities of various wavelengths emerging from the finger. It preferably has a first light source, which irradiates light through the finger, and a spectroscopic detector, which is sensitive to intensities of various wavelengths of light. A microprocessor then converts these measurements into a blood-alcohol concentration level and determines whether the level is at or above a threshold level. If the alcohol level is high, the interlock prevents the equipment from being operated. Operation of the equipment is preferably prevented by opening the equipment's ignition circuit, and may also be prevented by methods including preventing operation of an equipment starting mechanism, such as an engine starter, or, if the equipment is a vehicle, honking its horn and flashing its lights. If the alcohol level is lower than the threshold, the microprocessor causes an equipment operation switch, such as a relay to close the ignition circuit, permitting operation of the equipment.

The detector unit also has an identity detector, such as a fingerprint image generator. The image generator has a second light source, that reflects light off the finger, and a light sensor, such as a scanner. The scanner is sensitive to a reflected image of the finger's fingerprint. The microprocessor compares this image with a stored fingerprint image of the principal's fingerprint and determines whether the operator is in fact the principal operator.

To prevent different people's fingers from being used for the blood-alcohol detection and the fingerprint image generation, the two readings must occur substantially simultaneously for the microprocessor to permit operation of the equipment.

When the interlock is installed in a vehicle, the detection unit is preferably placed beneath the vehicle's driver's seat and is effectively only accessible to the vehicle operator, or driver.

DETAILED DESCRIPTION OF THE PREFERRED EMBODIMENTS

Figure 1:
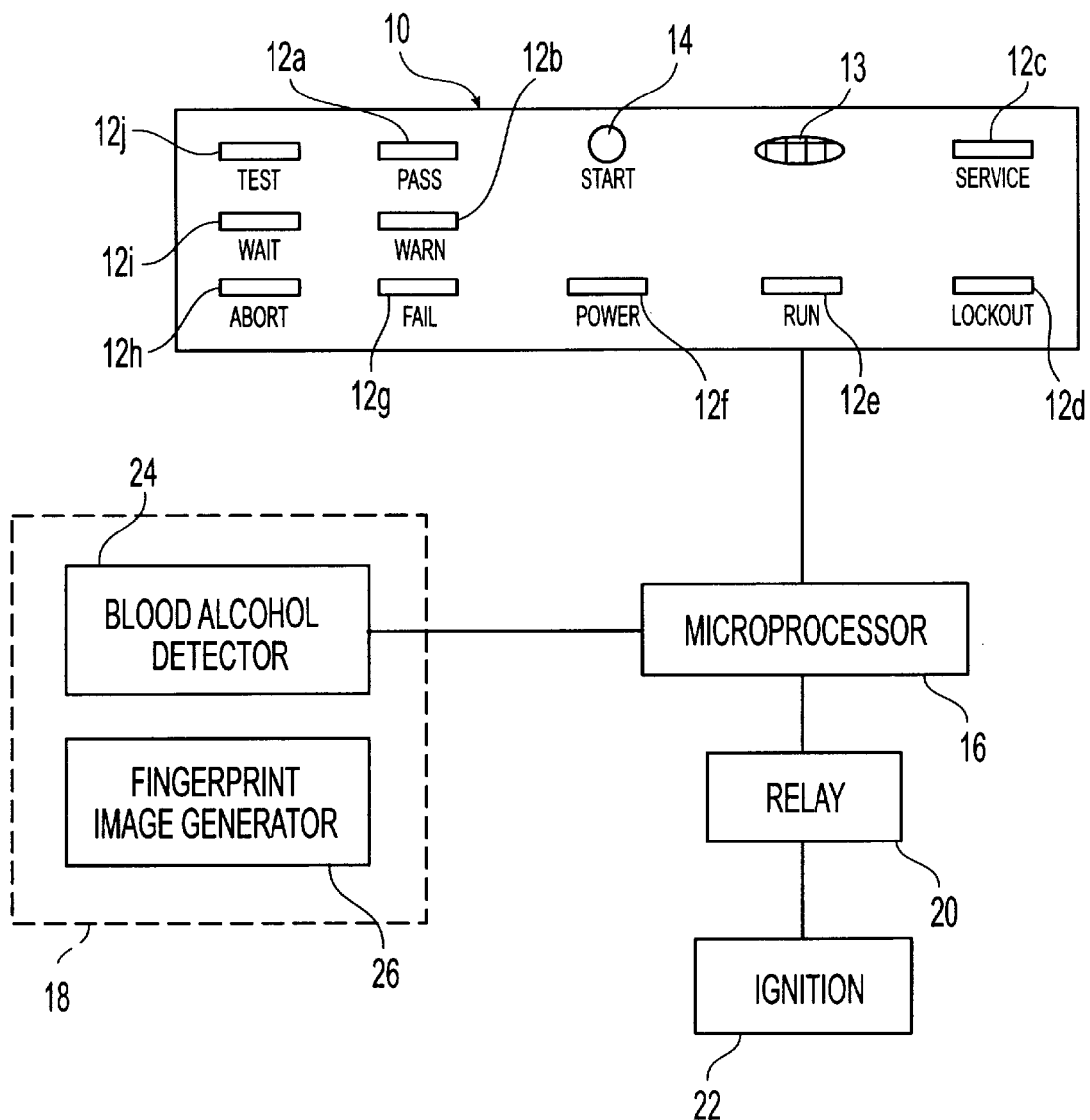
FIG. 1 diagrammatically illustrates an ignition interlock according to the invention.

FIG. 1 schematically represents the preferred embodiment of the ignition interlock of the invention. An annunciator panel 10 has a plurality of lights 12a–j that indicate the status of the interlock. The panel 10 also has a speaker 13 and a "start" button 14 to turn on the system and initiate a blood-alcohol test in order to start equipment in which the interlock is installed.

Annunciator panel 10 is electronically connected to a microprocessor 16 which electronically controls the functioning of the interlock and contains an information recording and storage medium, such as a magnetic cassette or disk in an appropriate drive, or other electronic volatile or nonvolatile memory. The microprocessor 16 is further connected to a detection unit 18 and a relay 20.

The relay 20 is switchable by the microprocessor 16 to open or close an ignition circuit 22 in the equipment. The ignition circuit 22 supplies electrical power necessary for the equipment to function. Thus, the equipment may only be started when the ignition circuit 22 is closed. When the circuit 22 is open, the equipment does not receive its electrical current needed to for it to run. Ignition circuit 22 may supply power to mechanisms such as starters or spark plugs.

The detection unit 18 contains a blood-alcohol detector 24 and a fingerprint image generator 26. The microprocessor 16 controls and processes the readings from each of these.

Figure 2:
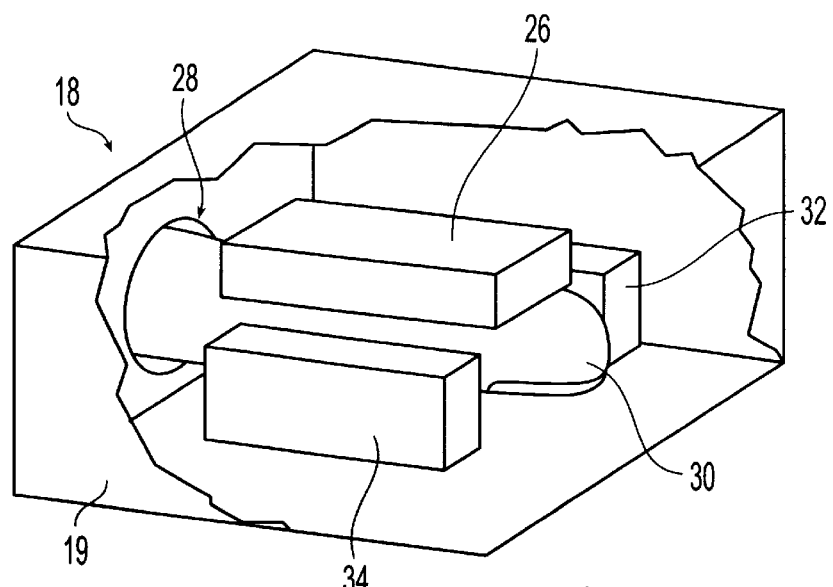
FIG. 2 is a perspective diagrammatic view of a detection unit according to the invention.

FIG. 2 is a perspective schematic view of the detection unit 18. The detection unit 18 has a housing 19 with a hole 28 through its side of suitable size to insert a bodypart therein, such as a finger 30. The blood-alcohol detector 24 has a first light source 32 and a spectroscopic detector 34 facing each other. When a finger 30 is inserted into the detection unit 18 through the hole 28, the first light source 32 and the detector 34 are disposed on opposite sides of the finger 30. Also inside the detection unit 18 is the fingerprint image generator 26, which is positioned to abut the underside of the fingertip of the inserted finger 30, which is shown facing upwards.

Figure 3:
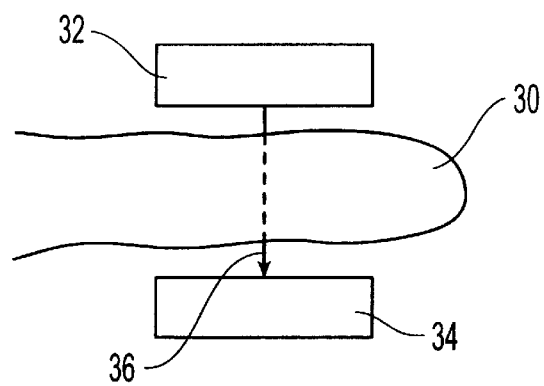
FIG. 3 illustrates the operation of a blood-alcohol detector according to the invention.

FIG. 3 schematically illustrates the operating blood-alcohol detector 24 as viewed from the top. This figure shows a first light source 32 emitting a preferably polychromatic light beam 36 through finger 30. The term "light" collectively refers to electromagnetic radiation both within and outside the visible spectrum. Light 36 is preferably in the near infrared region, encompassing wavelengths of about 650 nm to 2700 nm. The first light source 32 is preferably a tungsten-halogen lamp or one or more light emitting diodes.

A spectrographic detector 34 receives the light 36 emerging from the finger 30. The spectrographic detector 34 senses the intensity of different wavelengths of the emerging light 36, preferably through the use of a diffraction grating. Spectrographic detector 34 transmits this intensity information to the microprocessor 16.

The microprocessor 16 then applies a statistical algorithm that compares the intensity information with the intensity of the wavelengths emitted by the first light source 32 to determine the percentage of alcohol contained in the blood circulating through finger 30. Alcohol is known to have a sharp spectral absorbance at 1190 nm. The intensity of the emerging light 36 near this frequency is inversely related to the amount of alcohol in the blood in the path of the light 36. Thus, a high absorbance, or low intensity, registered by the spectrographic detector 34 and the microprocessor 16 near this wavelength indicates a high blood-alcohol content. In an alternative embodiment, the alcohol detector 24 and software of the microprocessor 16 are adapted to detect the presence of illegal drugs in the operator's blood stream. Suitable devices for spectroscopically measuring blood-alcohol content are also disclosed in U.S. Pat. Nos. 5,515,847, 5,435,309, and 5,361,758, which are herein incorporated by reference.

Figure 4:
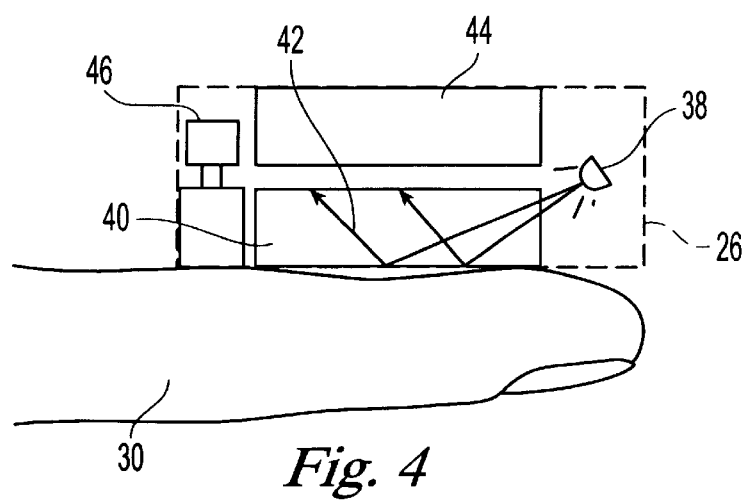
FIG. 4 illustrates the operation of a fingerprint image generator according to the invention.

The operation of the fingerprint image generator 26 is illustrated in FIG. 4. The operator places his or her finger 30 against the platen 40. The platen 40 is disposed above the finger 30 for easy access by an operator seated above the detection unit 18, with the palm of his or her hand facing the detection unit 18. This downwardly facing platen 40 position also improves its reliability as dirt and dust will not settle thereupon.

A second light source 38, such as a light emitting diode, directs light 42 through the platen 40, which is transparent to the wavelength of the light 42 employed. Light 42 reflects off the finger 30 and onto a scanner 44 which is sensitive to the light 42 and produces a scanned image of dark and light areas, which it electronically transmits to the microprocessor 16.

Microprocessor 16 then employs algorithms that identify distinctive features of the image and compare them to features of a prescanned image of the operator's fingerprint that is stored in the memory of the microprocessor 16. Such algorithms are taught in U.S. Pat. No. 5,067,162, which is herein incorporated by reference. Preferably, these algorithms do not require precise placement of the finger 30 on the platen 40. Thus, the microprocessor 16 determines whether or not the operator is the person whose fingerprint was originally recorded. Fingerprint imaging and devices usable in the present invention are also disclosed in U.S. Pat. Nos. 5,546,471, 5,467,403, and 5,088,817, which are herein incorporated by, reference.

Before the interlock system is utilized, an image of a primary operator's fingerprint is stored in the microprocessor's memory. When an operator wishes to start the equipment, he or she presses the "start" button 14 on the annunciator panel 10, energizing the interlock system. The system remains energized until a preselected time period has elapsed. When the energized system is ready to begin testing, a "test" light 12j on the annunciator panel 10 illuminates. At this point, the operator inserts his or her finger 30 through the hole 28 of the detection unit 18 and positions the finger 30 as shown in FIG. 2.

Once the system is energized, the microprocessor 16 activates both the blood-alcohol detector 24 and fingerprint image generator 26. When the microprocessor 16 detects both a finger print image and a light absorption reading that are within expected parameters for what a human finger would produce, the microprocessor 16 determines whether the measured blood-alcohol level is above or below the preprogrammed threshold value. The microprocessor 16 also has a comparator that compares the fingerprint image with the prestored image of the primary operator's fingerprint and determines whether the images sufficiently match and ascertains whether the analyzed finger 30 belongs to the primary operator.

The microprocessor 16 will determine that the test is passed if the blood-alcohol reading is below the threshold value and if the fingerprint image and the blood-alcohol reading have been acquired within a preselected, sufficiently short period so that the operator would not have enough time to remove his or her finger 30 and insert another object or finger. Preferably, this time period is sufficiently small that the fingerprint imaging and blood-alcohol measuring are effectively conducted simultaneously. This feature ensures that the fingerprint registered and the blood-alcohol reading come from the same person. Additionally, the microprocessor 16 is programmable so that the equipment can only be started if the fingerprint images do match.

Also, as an alternative to the blood-alcohol detector 24 and the fingerprint image generator 26 operating continuously once activated by microprocessor 16, an activation switch 46 can be provided to activate the alcohol detector 24 and the image generator 26, as shown in FIG. 4. When finger 30 presses against the activation switch 46 the systems within the detection unit 18 are activated.

Preferably, the light 36 traveling through the finger 30 and the reflected light 42 travel along paths that are generally perpendicular to each other so that the blood-alcohol and the fingerprint readings may be conducted at the same time without the two light beams 36 and 42 interfering with one another. Alternatively, the wavelengths of each light 36 and 42 are different, the detector 32 is not sensitive to the frequencies of the reflected light 42, and the scanner 44 is not sensitive to the light 36 of the blood-alcohol detector 24.

If the test is passed, the microprocessor 16 causes "pass" and "run" lights 12a and 12e to illuminate on the annunciator panel 10 to illuminate and activates the relay 20 that closes the ignition circuit, allowing the equipment to be started and operated. The microprocessor 16 records in its memory the blood-alcohol test results and whether or not the fingerprint images matched. If the results of the measured alcohol content in a passed test were below the preselected value but an amount of alcohol was detected anyway, a "warn" light 12b is illuminated instead of the "pass" light 12a.

If the result of the blood-alcohol measurement is inconclusive, the microprocessor 16 causes an "abort" light 12h to illuminate on the annunciator panel 10. Then the system resets itself for a new test.

If the test is failed because the measured blood-alcohol content is higher than the benchmark, the microprocessor 16 will illuminate a "fail" light 12g on the annunciator panel 10 and then reset the system for a new test. After a preselected number of test failures, preferably three, the system shuts off for a preselected shut off time period, preferably fifteen minutes, during which the "start" button 14 is inactive. If a test is failed, the interlock prevents the equipment from being operated. Manners in which equipment operation can be prevented include preventing it from starting, preventing it from running, or by creating a nuisance to an operator's continued running of the equipment. Such a nuisance can be generated by honking a loud horn on the equipment, or by flashing highly visible lights.

A "wait" light 12i is illuminated when the microprocessor 16 is preparing for a test, such as when the system is being reset between tests.

Figure 5:
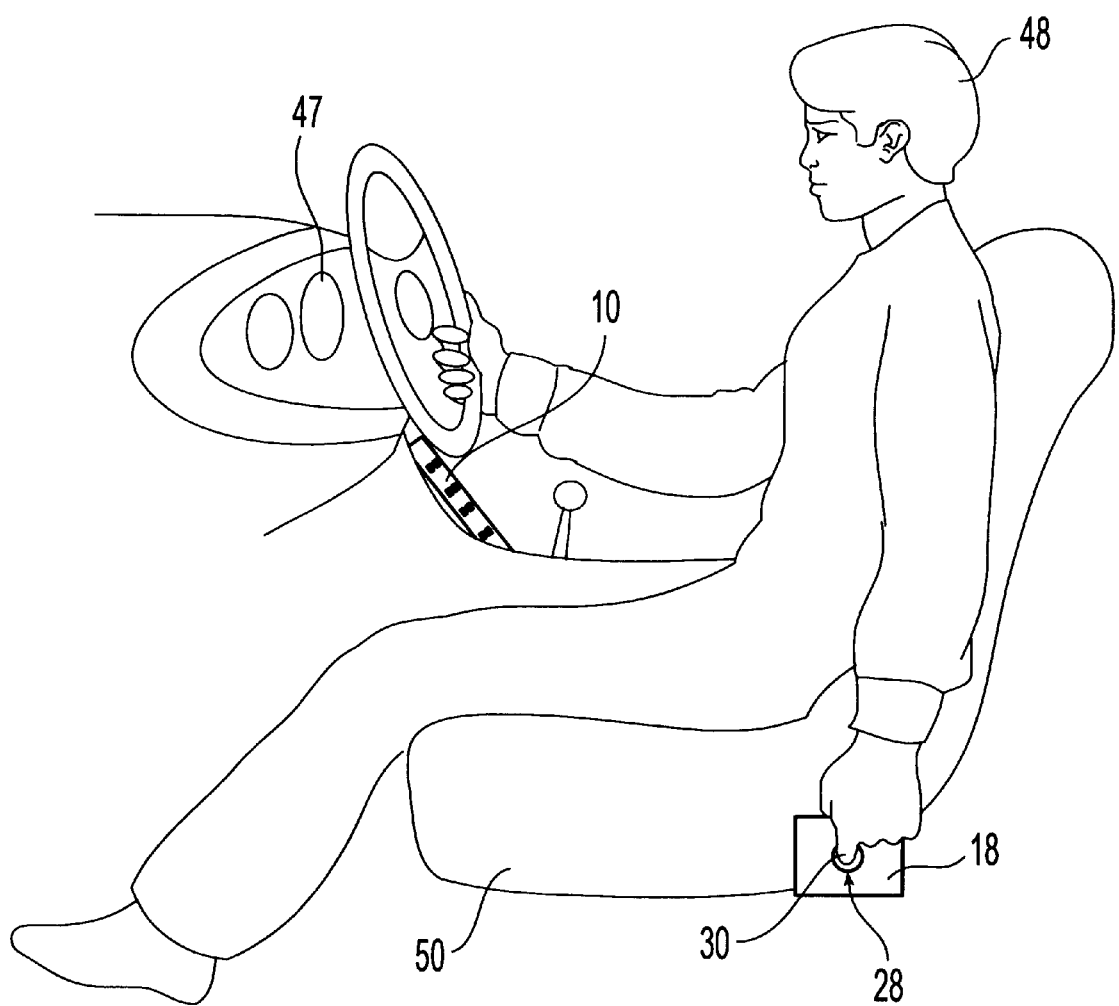
FIG. 5 shows an embodiment of the invention installed in an automobile.

FIG. 5 shows an embodiment of the invention installed in a motor vehicle. A driver 48 sits on the left side of the illustrated vehicle. The annunciator panel 10 faces the driver 48 on the console beneath the dashboard 47 for easy access and visibility. The detection unit 18 is installed beneath the driver's seat 50 towards the outside of the vehicle. In other words, where the driver's seat is on the left side of the vehicle, the detection unit 18 is located beneath the seat 50, on the left side.

The finger hole 28 in the detection unit 18 is oriented such that the driver may easily insert his or her finger 30 therein, but such that the hole 28 is effectively inaccessible to other vehicle occupants when the vehicle doors are closed or when the vehicle is in motion. In the illustrated position of the detection unit 18, the driver merely reaches down to his or her side to comfortably insert his or her finger 30 into hole 28 with the fingertip facing up, as shown in FIG. 2. Other vehicle passengers, on the other hand, would need to contort around the driver to reach the hole 28, and then twist their finger to properly seat it against platen 40. In vehicles that have back seats, the detection unit 18 is preferably located further forward than shown in FIG. 5 to hinder attempts by back seat passengers to reach the detection unit 18.

Once the vehicle has been started as previously described, the interlock system conducts random rolling retests to prevent the driver 48 from drinking after initial start-up and, if the microprocessor's program permits people other than the principal operator to start the vehicle, to discourage people other than the actual driver 48 from taking the test before the driver departs in the vehicle. At random time intervals, preferably between five to twenty five minutes, the system notifies the driver 48 that a retest is required by flashing the "test" light 12j and producing a beeping sound from the speaker of the annunciator panel 10.

Driver 48 must simply insert his or her finger 30 into the hole 28 of the detection unit 18 to take the test. If the driver 48 fails the test or does not take it during a thirty second time period, the microprocessor 16 leaves the relay 20 in its current state, permitting the engine to continue to run, but prevents normal operation of the vehicle by causing the vehicle's horn to sound repeatedly and the headlights to flash. To stop this, the driver 48 must either pass the test or turn off power to the engine, at which time the microprocessor 16 resets the relay 20 to turn off the ignition 22. Thereafter, the interlock will not permit vehicle restart until the driver 48 has taken and passed the test again.

In an alternative embodiment of the invention, the ignition circuit 22 merely controls a vehicle starter. Thus, the microprocessor 16 only closes the circuit 22 for a period of time, after which the microprocessor 16 opens the circuit again. In this embodiment, the vehicle will continue to run once it has been started and the circuit 22 has been opened.

The microprocessor 16 records in its memory relevant occurrences and the time they occurred. In addition to previously mentioned recorded data, the device records data including all test results, attempted starts, whether a rolling retest was taken within the allotted time, and system power supply changes and other data that indicate attempted tampering, such as whether the equipment has been started without the system having administered a test. The data stored in the memory can be accessed by, for example, a government agency requiring the use of the interlock system.

What is claimed:

1. A method for preventing equipment having an operator seat from being operated comprising:
   mounting a non-breathalizer blood-alcohol detector adapted to receive a bodypart under the operator's seat;
   receiving a bodypart in the blood-alcohol detector;
   detecting blood-alcohol concentration of the bodypart through tissue of said bodypart;
   comparing the detected blood-alcohol concentration to a preselected threshold value; and
   preventing operation of the equipment when the detected blood-alcohol concentration is at least the threshold value.

2. The method of claim 1, wherein the step of preventing operation of the equipment comprises preventing the equipment from being started.

3. The method of claim 1, wherein the step of detecting the blood-alcohol content comprises measuring light emerging from the bodypart.

4. The method of claim 3, wherein the step of measuring the light comprises measuring intensities of wavelengths of the light emerging from the bodypart.

5. The method of claim 4, further comprising the step of irradiating the bodypart to generate the wavelengths of light that are measured.

6. The method of claim 4, further comprising the steps of:
   storing data corresponding to a distinguishing aspect that corresponds to the identity of a principal equipment operator;
   measuring the distinguishing aspect from the bodypart;
   comparing said stored data to said measured aspect; and
   determining and whether said stored data and said measured aspect match.

7. The method of claim 6, further comprising the step of preventing operation of the equipment unless the stored data and the measured aspect match.

8. The method of claim 6, wherein said step of measuring the distinguishing aspect occurs substantially simultaneously with the step of detecting the blood-alcohol content.

9. The method of claim 6, wherein the bodypart is a finger, the blood-alcohol detector is shaped to receive the finger, and the distinguishing aspect is a fingerprint.

10. The method of claim 9, further comprising the steps of reflecting light off the finger and scanning the reflected light to form an image of a fingerprint from the finger.

11. The method of claim 10, wherein said reflected light and the light emerging from the finger travel in directions generally perpendicular to each other.

12. The method of claim 10, wherein the reflected light and the light emerging from the finger have different wavelengths.

13. A method for preventing a vehicle from being operated, comprising:
    mounting a housing shaped to receive a finger under a driver's seat of the vehicle;
    receiving the finger in the housing;
    detecting blood-alcohol concentration of the finger through tissue of said finger;
    comparing the detected blood-alcohol concentration to a preselected threshold value; and
    preventing operation of the vehicle when the detected blood-alcohol concentration is at least the threshold value.

14. A method for preventing a vehicle from being operated comprising:
    mounting a finger print detector adapted to receive a finger under a driver's seat of the vehicle;
    receiving the finger in the finger print detector;
    storing data corresponding to a fingerprint of a principal vehicle-driver;
    measuring the a fingerprint from a finger;
    comparing the stored fingerprint to the measured fingerprint;
    determining whether the stored and measured fingerprints match; and
    preventing operation of the vehicle unless the stored and measured fingerprints match.

15. An ignition interlock for a vehicle, comprising:
    a blood-alcohol detector sensitive to a blood-alcohol concentration of a bodypart and capable of detecting the blood-alcohol concentration without reliance on breath-alcohol information, wherein the blood-alcohol detector is disposed in the vehicle in a location disposed for restricting access by a non-driver of the vehicle when a driver is seated in a driver's seat of the vehicle;
    electronic circuitry connected to the blood alcohol-detector and configured for comparing the detected blood-alcohol concentration to a preselected threshold value; and
    an operation switch connected to the electronic circuitry and capable of preventing operation of the vehicle when the detected blood-alcohol concentration is at least the threshold value.

16. The interlock of claim 15, wherein the blood-alcohol detector includes a spectroscopic detector for measuring light emerging from the bodypart.

17. The interlock of claim 16, the spectroscopic detector is configured to measure intensities of wavelengths of the light emerging from the bodypart.

18. The interlock of claim 17, further comprising a first light source for irradiating the bodypart to generate the wavelengths of light that are measured.

19. The interlock of claim 17, further comprising an identity detector for measuring a distinguishing aspect from the bodypart, wherein the electronic circuitry has a memory, data stored in the memory corresponding to the distinguishing aspect that corresponds to the identity of a principal equipment operator, and a comparator for comparing said stored data to said measured aspect and determining whether the stored data and the measured aspect match.

20. The interlock of claim 19, further comprising an activation switch configured to activate the identity and blood-alcohol detector when depressed by the bodypart.

21. The interlock of claim 19, wherein the electronic circuitry includes a prevention program for preventing operation of the equipment unless the stored data and the measured aspect match.

22. The interlock of claim 19, wherein electronic circuitry is configured to conduct the measurement of the distinguishing aspect substantially simultaneously with the detection of the blood-alcohol content.

23. The interlock of claim 19, wherein the bodypart is a finger and the distinguishing aspect is a fingerprint.

24. The interlock of claim 23, wherein the identity detector has a second light source and a light sensor, the second light source being aimed for reflecting light off the finger and onto the light sensor, and the light sensor forming an image of the fingerprint and transmitting said image to the microprocessor.

25. The interlock of claim 24, wherein the light reflected off the finger and the light emerging from the finger travel in directions substantially perpendicular to each other.

26. The interlock of claim 24, wherein the light reflected off the finger and the light emerging from the finger have different wavelengths.

27. The interlock of claim 24, further comprising housing shaped to receive a finger, the housing containing said identity and blood-alcohol detectors, wherein the equipment is a vehicle and the housing is disposed under a vehicle driver's seat.

28. The interlock of claim 15, wherein the electronic circuitry comprises a microprocessor.

29. The method of claim 1, wherein the equipment is a vehicle, the bodypart is a finger, and the detecting of the blood-alcohol concentration in the bodypart is conducted under the driver seat of the vehicle.

30. The method of claim 1, wherein the preventing operation of the equipment comprises operating a switch to prevent operation of the equipment when the detected blood-alcohol concentration is at least the threshold value.

31. The method of claim 15, wherein the equipment is a vehicle, the blood-alcohol detector is located under a vehicle driver seat, and the bodypart is a finger.

32. An interlock for equipment having an operator seat, comprising:

a non-breathalizer blood-alcohol detector disposed under the operator seat and configured to receive a finger, the blood-alcohol detector sensitive to a blood-alcohol concentration of the finger and capable of detecting the blood-alcohol concentration;

electronic circuitry connected to the blood alcohol-detector and configured for comparing the detected blood-alcohol concentration to a preselected threshold value; and an operation switch connected to the electronic circuitry and capable of preventing operation of the equipment vehicle when the detected blood-alcohol concentration is at least the threshold value.

33. The interlock of claim 32, wherein the equipment is a vehicle and the operator's seat comprises a driver's seat.

34. The interlock of claim 33, wherein the blood-alcohol detector is oriented for receiving the bodypart on a side of the driver's seat facing towards the outside of the vehicle.

35. The interlock of claim 32, further comprising a finger print detector for measuring a fingerprint from the finger, wherein the electronic circuitry has a memory, data stored in the memory corresponding to the finger of a principal equipment operator, and a comparator for comparing said stored data to said fingerprint and determining whether the stored data and the fingerprint match.

* * * * *